United States Patent [19]
Yoon

[11] Patent Number: 5,466,224
[45] Date of Patent: Nov. 14, 1995

[54] SAFETY PENETRATING INSTRUMENT HAVING A TRIGGERED PORTAL SLEEVE FOR ESTABLISHING AN ENDOSCOPIC PORTAL IN AN ANATOMICAL CAVITY WALL

[76] Inventor: InBae Yoon, 2101 Highland Ridge Dr., Phoeniz, Md. 21131

[21] Appl. No.: 83,728

[22] Filed: Jun. 29, 1993

Related U.S. Application Data

[63] Continuation-in-part of Ser. No. 628,899, Dec. 18, 1990, Pat. No. 5,226,426, and a continuation-in-part of Ser. No. 817,113, Jan. 6, 1992, Pat. No. 5,350,393.

[51] Int. Cl.⁶ ........................................... A61M 5/00
[52] U.S. Cl. ........................... 604/165; 604/274; 606/185
[58] Field of Search .................................. 128/751, 752, 128/753, 754, 4, 6; 604/95, 158, 162, 163, 164, 165, 169, 170, 272, 274, 280; 606/167, 170, 171, 185

[56] References Cited

U.S. PATENT DOCUMENTS

| | | |
|---|---|---|
| 1,087,845 | 2/1914 | Stevens . |
| 1,213,001 | 1/1917 | Phillips . |
| 1,248,492 | 12/1917 | Hill . |
| 1,527,291 | 2/1925 | Zorraquin . |
| 2,496,111 | 1/1950 | Turkel . |
| 2,623,521 | 12/1952 | Shaw . |
| 2,630,803 | 3/1953 | Baran . |
| 4,254,762 | 3/1981 | Yoon . |
| 4,535,773 | 8/1985 | Yoon . |
| 4,601,710 | 7/1986 | Moll . |
| 4,654,030 | 3/1987 | Moll et al. . |
| 4,828,547 | 5/1989 | Sahi et al. . |
| 4,869,717 | 9/1989 | Adair . |
| 4,902,280 | 2/1990 | Lander . |
| 4,931,042 | 6/1990 | Holmes et al. . |
| 4,943,280 | 7/1990 | Lander . |
| 5,053,016 | 10/1991 | Lander . |
| 5,066,288 | 11/1991 | Denieqa et al. . |
| 5,073,169 | 12/1991 | Raiken . |
| 5,104,382 | 4/1992 | Brinkerhoff et al. . |
| 5,104,383 | 4/1992 | Shichman . |
| 5,114,407 | 5/1992 | Burbank . |
| 5,116,353 | 5/1992 | Green . |
| 5,122,122 | 6/1992 | Allgood . |
| 5,127,909 | 7/1992 | Shichman . |
| 5,152,754 | 10/1992 | Plyley et al. . |
| 5,158,552 | 10/1992 | Borgia et al. . |
| 5,207,647 | 5/1993 | Phelps . |
| 5,215,526 | 1/1993 | Denieqa et al. . |
| 5,224,951 | 7/1993 | Freitas . |

(List continued on next page.)

FOREIGN PATENT DOCUMENTS

| | | |
|---|---|---|
| 2544262 | 4/1977 | Germany . |
| 878265 | 11/1981 | U.S.S.R. . |
| 897224 | 1/1982 | U.S.S.R. . |
| 1435246 | 11/1988 | U.S.S.R. . |
| 904635 | 8/1962 | United Kingdom . |
| 9304632 | 3/1993 | WIPO . |
| 9304715 | 3/1993 | WIPO . |
| 9304716 | 3/1993 | WIPO . |
| 9317626 | 3/1993 | WIPO . |

*Primary Examiner*—Stephen C. Pellegrino
*Assistant Examiner*—Guy V. Tucker

[57] ABSTRACT

A safety penetrating instrument for establishing a portal in an anatomical cavity for performing endoscopic procedures includes a penetrating member received within a distally biased portal sleeve for introducing the portal sleeve through a cavity wall into the anatomical cavity, the portal sleeve having a distal end movable between an extended position protecting a sharp tip of the penetrating member and a retracted position exposing the sharp tip. A handle is provided manually moving the portal sleeve to the retracted position, and a locking and releasing mechanism locks the portal sleeve in the retracted position and releases the portal sleeve to return to the extended position in response to distal movement of an operating member upon penetration of the safety penetrating instrument into the anatomical cavity, the operating member being preferably carried by the penetrating member.

17 Claims, 10 Drawing Sheets

U.S. PATENT DOCUMENTS

| | | |
|---|---|---|
| 5,224,952 | 7/1993 | Deniega et al. . |
| 5,226,891 | 7/1993 | Bushatz et al. . |
| 5,246,425 | 9/1993 | Hunsberger et al. . |
| 5,248,298 | 9/1993 | Bedi et al. . |
| 5,256,148 | 10/1993 | Smith et al. . |
| 5,256,149 | 10/1993 | Banik et al. . |
| 5,261,891 | 11/1993 | Brinkerhoff et al. . |
| 5,267,965 | 11/1993 | Deniega . |
| 5,275,583 | 1/1994 | Crainich . |
| 5,290,243 | 3/1994 | Chodorow et al. ............ 604/165 |
| 5,290,304 | 3/1994 | Storace ............................ 606/184 |
| 5,295,993 | 3/1994 | Green ............................... 606/184 |
| 5,312,354 | 5/1994 | Allen et al. ..................... 604/157 |

SAFETY PENETRATING INSTRUMENT HAVING A TRIGGERED PORTAL SLEEVE FOR ESTABLISHING AN ENDOSCOPIC PORTAL IN AN ANATOMICAL CAVITY WALL

CROSS REFERENCE TO RELATED APPLICATIONS

This application is a continuation-in-part of application Ser. No. 07/628,899, filed Dec. 18, 1990, now U.S. Pat. No. 5,266,426, and patent application Ser. No. 07/817,113, filed Jan. 6, 1992, now U.S. Pat. No. 5,350,393 the disclosures of which are incorporated herein by reference.

BACKGROUND OF THE INVENTION

1. Field of the Invention

The present invention pertains to safety penetrating instruments and, more particularly, to safety penetrating instruments for use in forming portals for endoscopic procedures having safety members spring biased to an extended protruded position to protect against inadvertent contact with tissue of sharp penetrating members.

2. Discussion of the Prior Art

Safety penetrating instruments are widely used in medical procedures to gain access to anatomical cavities for performing endoscopic procedures, particularly laparoscopic procedures in the anatomical cavity. A well accepted type of safety penetrating instrument, as exemplified by U.S. Pat. No. 4,535,773 to Yoon, the Endopath trocar marketed by Ethicon EndoSurgery and the Surgiport trocar marketed by United States Surgical Corporation, includes a portal sleeve or cannula, a penetrating member received in the portal sleeve and a safety shield spring biased to move to an extended, protruding position to cover the sharp tip of the penetrating member once the penetrating member has entered the anatomical cavity. Accordingly, the safety shield protects tissue and organ structures within the anatomical cavity from accidental injury by contact with the sharp tip of the penetrating member after penetration or puncture of the anatomical cavity wall.

When the penetrating procedure is commenced, the distal end of the safety penetrating instrument is placed in contact with the anatomical cavity wall; and, as force is exerted on the safety penetrating instrument, contact of the safety shield with the cavity wall moves the safety shield proximally to a retracted position against the spring bias to expose the sharp tip of the penetrating member to permit the sharp tip to penetrate the cavity wall. Accordingly, the force required to penetrate the cavity wall includes not only the force required to pass the safety penetrating instrument through the anatomical cavity wall but also the force required to overcome the spring bias on the safety shield. Once the sharp tip of the penetrating member has entered the cavity, the spring bias on the safety shield overcomes the reduced proximal force on the safety shield causing the safety shield to move distally to the extended, protruding position, In practice, however, a residual proximal force is still applied to the safety shield after penetration of the sharp tip into the cavity due to contact with surrounding tissue and/or tissue trapped between the safety shield and the portal sleeve and/or the penetrating member, and the residual force is capable of preventing distal movement of the safety shield to the extended position. To assure distal movement of the safety shield upon entry of the safety penetrating instrument into the anatomical cavity, the strength of the spring biasing the safety shield distally can be increased; however, increasing the strength of the bias spring also increases the force required to penetrate the cavity wall which is undesirable. Accordingly, currently available safety penetrating instruments with safety shields utilize bias springs of strengths compromising force-to-penetrate and assured safety shield distal movement in an attempt to satisfy both requirements.

In order to provide surgeons with a sense of security, currently available safety penetrating instruments with safety shields utilize a mechanism for locking the safety shield in the distally protruded position after entry into the anatomical cavity; however, the need for a locking mechanism from a purely medical standpoint is not well established in that it is possible that a locked safety shield could cause damage upon inadvertent contact with tissue whereas an unlocked safety shield would move proximally against the spring bias like a shock absorber. It would be desirable to provide a safety penetrating instrument that provides both a sense of security to the surgeon and a shock absorbing effect.

While currently available safety penetrating instruments with safety shields have been well received by surgeons for use in endoscopic procedures, there is room for improvement due to the compromise required in selecting the strength of the spring distally biasing the safety shield, to the increased force-to-penetrate required by the addition of the safety shield, as compared to a penetrating instrument formed of only a penetrating member and a portal sleeve, and to premature movement of the safety shield to the extended position protecting the sharp penetrating member tip before the distal end of the portal sleeve has entered the anatomical cavity. In the latter case, distal movement of the safety shield indicates to the surgeon that penetration has been completed; however, if the safety shield is removed after premature movement to the extended position, the portal sleeve will not provide a portal communicating with the anatomical cavity; and, if fluid such as insufflation gas is introduced through the portal sleeve, peritoneal emphysema can result.

SUMMARY OF THE INVENTION

Accordingly, it is a primary object of the present invention to improve safety penetrating instruments of the type where the sharp distal end of a penetrating member is covered or shielded after penetration into an anatomical cavity by reducing the force-to-penetrate and assuring entry of the portal sleeve into the anatomical cavity.

Another object of the present invention is to reduce the force-to-penetrate required to penetrate an anatomical cavity wall with a safety penetrating instrument while assuring shielding of a sharp distal end of a penetrating member once penetration into the cavity has been achieved.

A further object of the present invention is to form a safety penetrating instrument of a penetrating member and a portal sleeve biased to move distally in response to distal movement of an operating member upon entry of the safety penetrating instrument into an anatomical cavity, the portal sleeve having a distal end protruding beyond the sharp distal tip of the penetrating member to protect against inadvertent contact with tissue in the anatomical cavity and act as a safety member.

The present invention has an additional object in that a distally biased portal sleeve is locked in a retracted position to expose a sharp distal end of a penetrating member prior to contacting a wall of an anatomical cavity to be penetrated and is released to allow movement of the portal sleeve to an extended position upon penetration into the anatomical cavity.

Another object of the present invention is to trigger release of a distally biased portal sleeve in response to distal movement of a penetrating member upon penetration into an anatomical cavity.

A further object of the present invention is to utilize a strong spring to distally bias a portal sleeve in a safety penetrating instrument to provide a shock absorber or cushion action and to assure distal movement of the portal sleeve through the anatomical cavity wall to the extended position protecting the sharp penetrating member tip without increasing the force-to-penetrate of the safety penetrating instrument.

Some of the advantages of the safety penetrating instrument of the present invention over the prior art are that the distal biasing force on the portal sleeve can be designed to assure protrusion upon penetration regardless of the anatomical cavity being penetrated, that the force-to-penetrate of the safety penetrating instrument is minimized, that the safety penetrating instrument provides safe penetration without requiring an extra component to act as a safety member, and that the safety penetrating instrument can be inexpensively manufactured with minimum components to reduce cost, facilitate sterilization for reuse and allow economical, single patient use.

The present invention is generally characterized in a safety penetrating instrument for establishing a portal in a wall of an anatomical cavity for performing endoscopic procedures including a portal sleeve having a distal end for positioning in the anatomical cavity and a proximal end for positioning externally of the anatomical cavity wall, a penetrating member disposed in the portal sleeve having a sharp distal end for penetrating tissue, a housing mounting the portal sleeve to be movable relative to the penetrating member between an extended position where the portal sleeve distal end protrudes distally of the penetrating member sharp distal end and a retracted position where the portal sleeve distal end is disposed proximally of the penetrating member sharp distal end to expose the penetrating member sharp distal end, bias means for biasing the portal sleeve to move distally toward the extended position and for permitting the portal sleeve to move proximally toward the retracted position, a handle coupled with the portal sleeve for moving the portal sleeve to the retracted position, locking means for engaging the portal sleeve to lock the portal sleeve in the retracted position and releasing means including an operating member responsive to entry of the safety penetrating instrument into the anatomical cavity for triggering release of the locking means to permit the bias means to move the portal sleeve to the extended position.

The above and still further objects, features and advantages of the present invention will become apparent from the following description of the preferred embodiments when considered in conjunction with the accompanying drawings wherein like reference numerals in the various figures are utilized to designate like components.

DESCRIPTION OF THE PREFERRED EMBODIMENT

Figure 1:
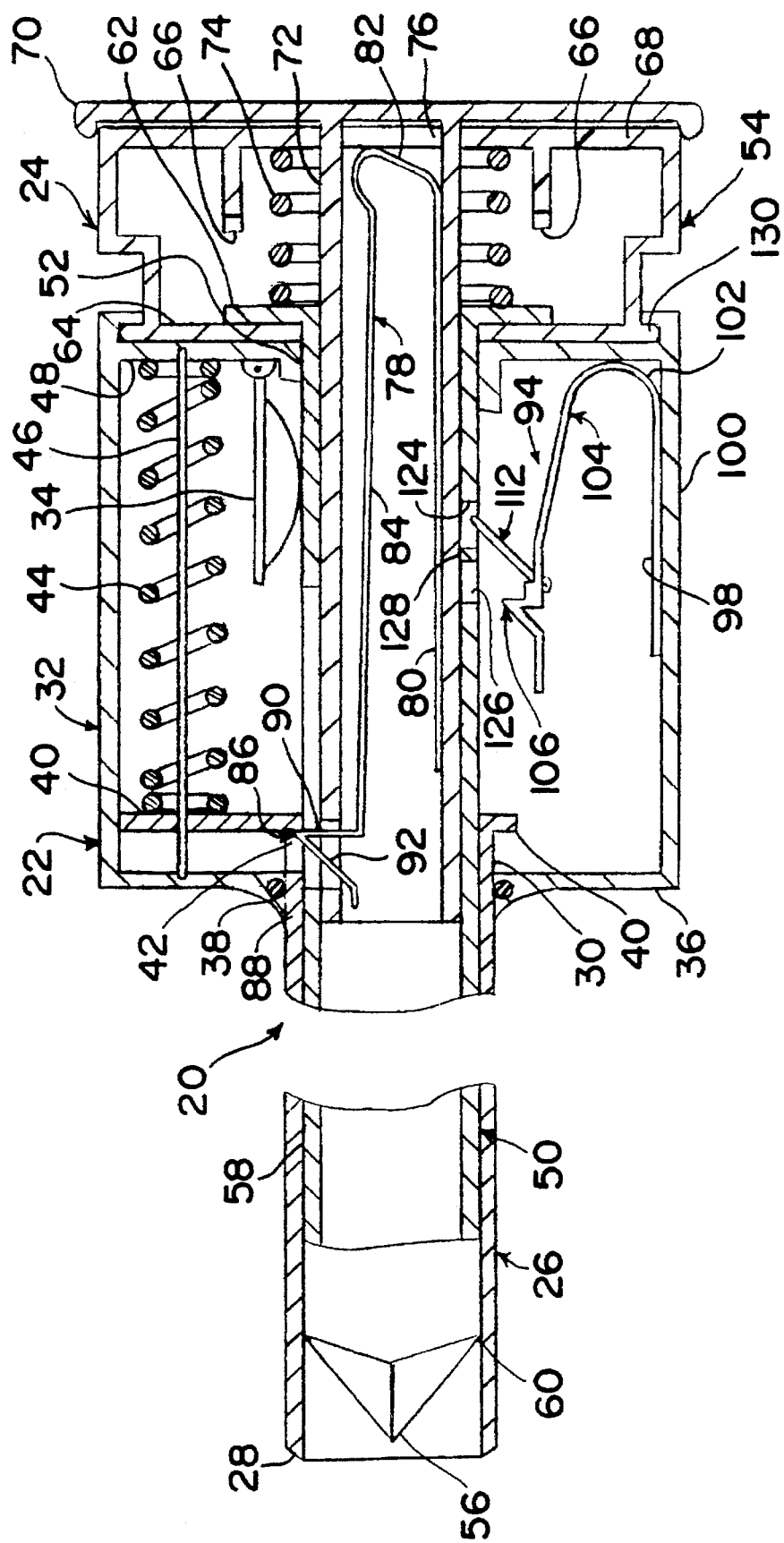
FIG. 1 is a broken longitudinal section of a safety penetrating instrument according to the present invention with the portal sleeve in an extended, distally protruding position.

A safety penetrating instrument 20 according to the present invention, as shown in FIG. 1, is formed of a portal unit 22 and a penetrating unit 24. The portal unit 22 includes an elongate, cylindrical portal sleeve or cannula 26 having a distal end 28 and a proximal end 30 movably received in a housing 32. The housing 32 is preferably constructed to sealingly engage instruments passing therethrough and to include a valve 34 biased to a closed state when no instrument passes through the portal sleeve. A flapper valve 34 is shown; however, any suitable valve construction can be utilized, for example, trumpet or nipple valves. Portal sleeve 26 slidably extends through a front wall 36 of housing 32 in engagement with a seal, such as an O-ring 38; and, the proximal end 30 of the portal sleeve terminates at a transversely extending flange 40 adjacent a slot or notch 42. A helical spring 44 is coiled around a guide rod 46 passing through an upper portion of flange 40 and mounted in compression between flange 40 and a rear wall 48 of the housing 32 to distally bias portal sleeve 26 to the extended position shown in FIG. 1.

The penetrating unit 24 includes an elongate penetrating member 50 having a proximal end 52 received in a hub 54, a sharp distal end or tip 56, and a shaft 58 extending between the proximal and distal ends. The distal end can have any configuration desired by a surgeon for a particular procedure, for example, the pyramidal trocar configuration shown having facets extending from the tip to a junction 60 with the shaft 58, or conical, threaded, multi-faceted or open, slanted configurations. The penetrating member can be made of multiple components such that the distal tip 56 is interchangeably engaged with the shaft 58, for example by threaded engagement. The proximal end 52 of penetrating instrument 50 is hollow and terminates at a transversely extending flange 62 movable between a front wall 64 of the hub and stops 66 extending from a rear wall 68 of the hub.

A handle 70 is positioned in abutment with hub rear wall 68 and mounts a guide tube 72 concentric with the longitudinal axis of the safety penetrating instrument to be received in the open proximal end 52 of the penetrating member to allow the penetrating member to slide over the guide tube against the bias of a helical spring 74 coiled around guide tube 72 and mounted in compression between flange 62 and hub rear wall 68. The hub rear wall 68 has a passage 76 therein for receiving guide tube 72 in sliding engagement allowing handle 70 to be moved along the axis of the safety penetrating instrument. A locking member 78 is mounted within guide tube 72 and is formed of a strip of resilient material having a base 80 mounted in the guide tube and a bend 82 joining the base with an arm 84 carrying a lock protrusion 86 having an angled distal surface 88 and a locking surface 90 extending substantially transversely from the longitudinal axis of the safety penetrating instrument. Guide tube 72 has a slot 92 aligned with slot or notch 42 when the portal sleeve 26 is in the extended position such that lock 86 extends through slot 92 and into slot 42 to hold the portal sleeve in the extended position.

Figure 2:
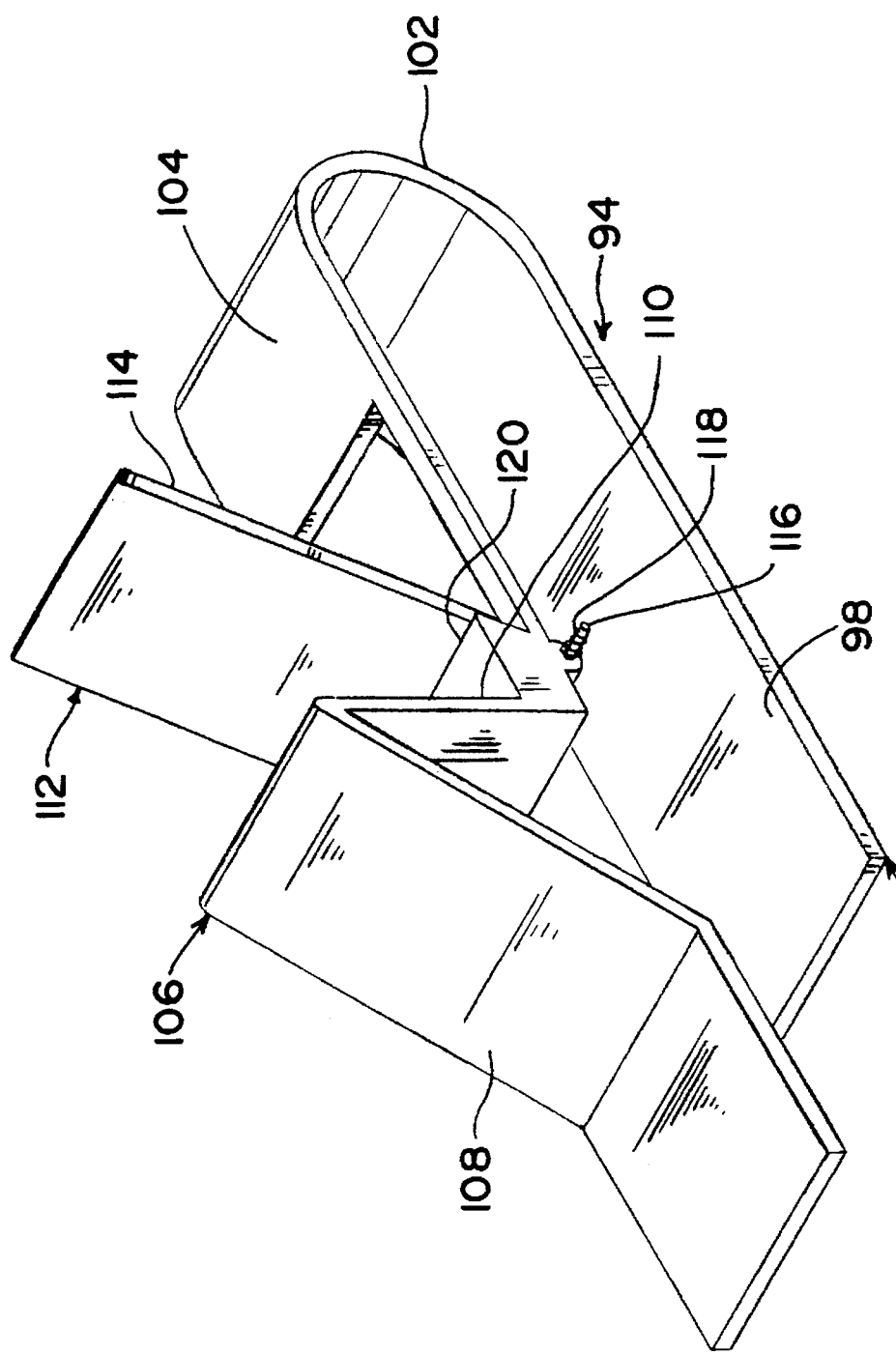
FIG. 2 is a perspective view of a locking and releasing mechanism for the safety penetrating instrument of FIG. 1.

A locking and releasing mechanism 94 for locking the portal sleeve in a retracted position exposing the sharp distal end 56 of the penetrating member and releasing the portal sleeve to allow the portal sleeve to return to the extended position includes a latch or locking spring 96 made of a strip of resilient material formed to have a substantially flat base 98 secured to a bottom wall 100 of housing 32 and a bend 102 joining the base 98 with an arm 104 spaced from the base, as shown in FIG. 2. Arm 104 carries a protruding latch 106 having a distal angled surface 108 joining a proximal latching surface 110 disposed substantially transversely to the longitudinal axis of the safety penetrating instrument and substantially parallel to the portal sleeve flange 40. A trigger 112 is formed by a leg 114 having an end pivotally mounted on a pin 116 on arm 104, and a spring 118 biases the trigger 112 counterclockwise against a protrusion 120 disposed adjacent leg 114 of the trigger to limit counterclockwise pivotal movement of the trigger away from arm 104 while clockwise pivotal movement of the trigger is permitted against the bias of the spring. Trigger leg 114 has an opposing end extending into a slot or notch 124 in penetrating member 50, and slot 124 is separated from a slot or notch 126 in the penetrating member by an operating member 128.

The portal unit 22 and the penetrating unit 24 can be provided to a surgeon separately or assembled together as shown in FIG. 1, and either or both of the portal and penetrating units can be manufactured in a manner to be disposable for single patient use or to be sterilizable for reuse. The hub 54 can be coupled to the housing 32 by any suitable detent or latch mechanism as shown at 130.

Figure 3:
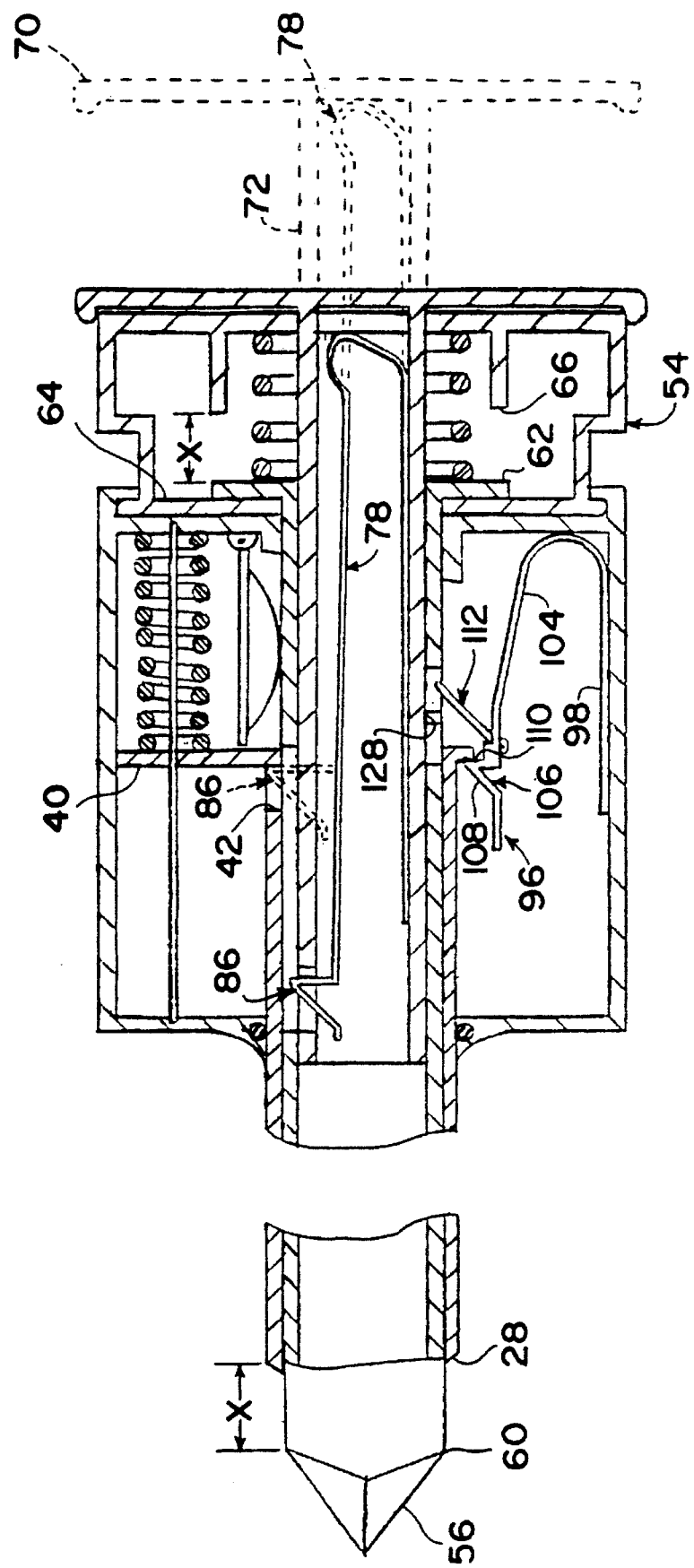
FIG. 3 is a broken longitudinal section of the safety penetrating instrument of FIG. 1 with the portal sleeve in a locked retracted position.

In use, the safety penetrating instrument 20 will initially be in the position shown in FIG. 1 with portal sleeve 26 in an extended position such that the distal end 28 of the portal sleeve protrudes beyond the sharp distal end 56 of the penetrating member. Prior to commencing penetration of an anatomical cavity wall W, handle 70 is grasped and manually moved proximally to the position shown in phantom in FIG. 3, the proximal movement of the handle moving the portal sleeve proximally due to engagement of lock 86 in slot 42. Flange 40 will ride over angled distal surface 108 of the locking and releasing mechanism until flange 40 rides over latch 106 by engaging angled distal surface 108 to move arm 104 toward base 98. At this time, the surgeon can feel the flange 40 lock into place in engagement with latching surface 110 as arm 104 springs back. The safety penetrating instrument 20 is now in the position illustrated in FIG. 3 with the portal sleeve locked in the retracted position by locking and releasing mechanism 96 and the sharp distal tip 56 of the penetrating member exposed with junction 60 spaced from the distal end 28 of the portal sleeve by a distance X which is substantially the same as the distance X between flange 62 and stop 66. The penetrating member is biased distally such that flange 62 is adjacent the front wall 64 of hub 54 and operating member 128 is disposed distally of trigger 112.

Figure 4:
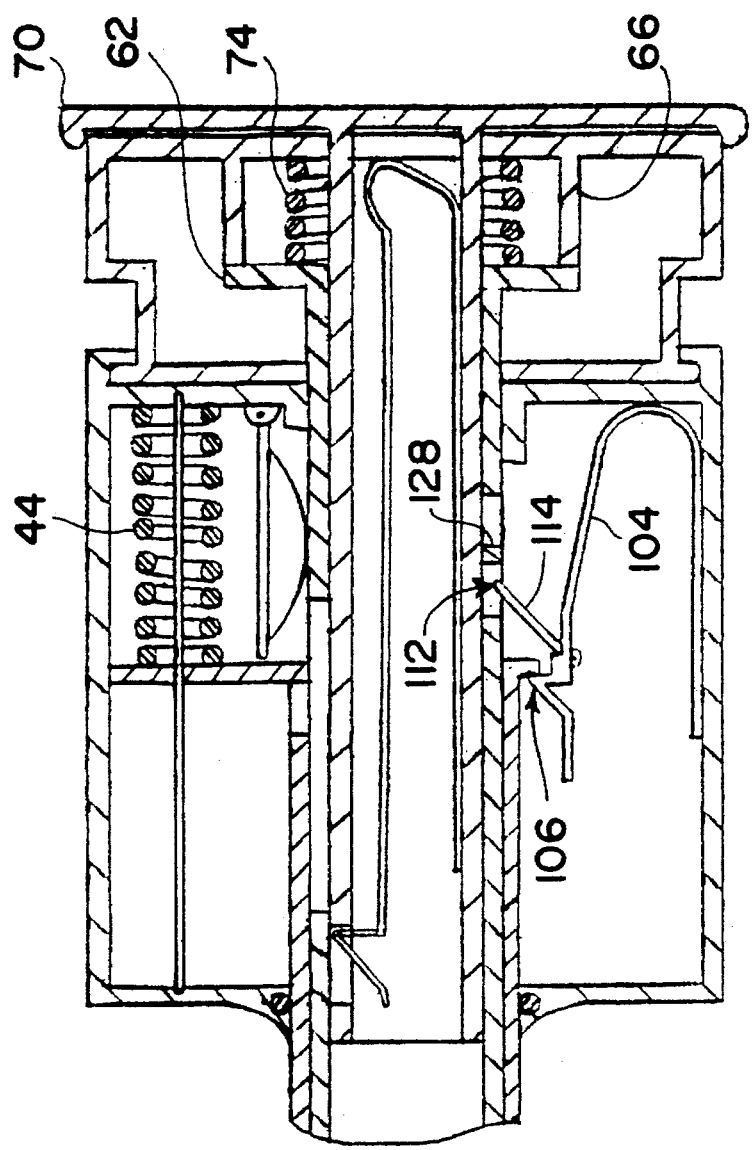
FIG. 4 is a broken longitudinal section of the safety penetrating instrument of FIG. 1 with the penetrating member moved proximally during penetration of an anatomical cavity wall.
Figure 4:
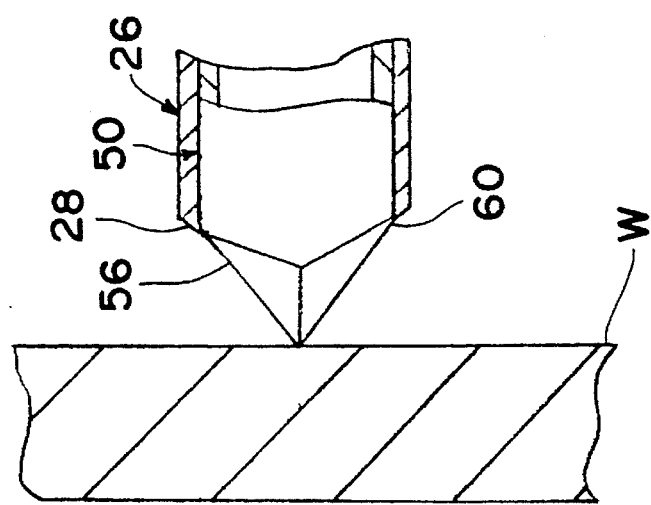
Figure 5:
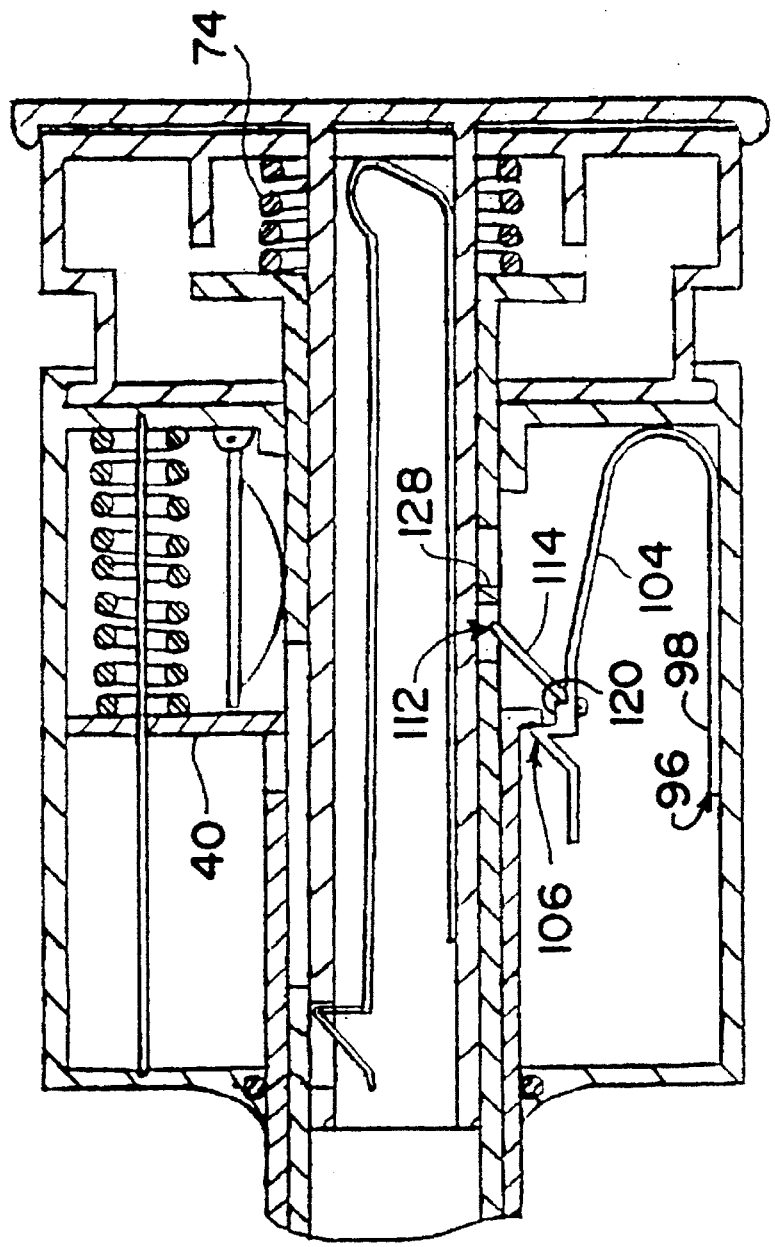
FIG. 5 is a broken longitudinal section of the safety penetrating instrument of FIG. 1 with the penetrating member moved distally to release the portal sleeve.
Figure 5:
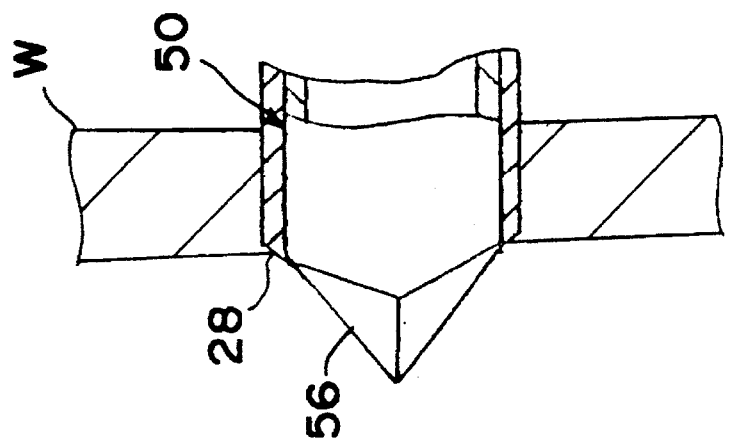
Figure 6:
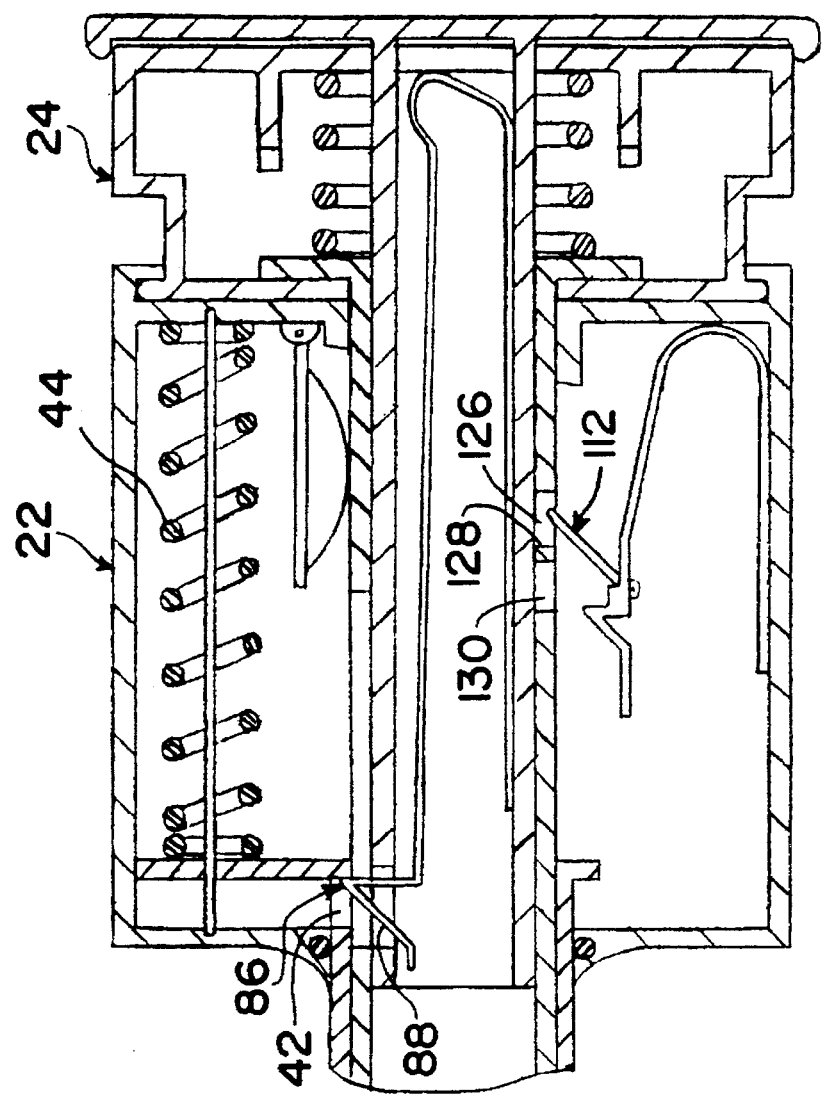
FIG. 6 is a broken longitudinal section of the safety penetrating instrument of FIG. 1 with the portal sleeve in the extended position after penetrating into an anatomical cavity.
Figure 6:
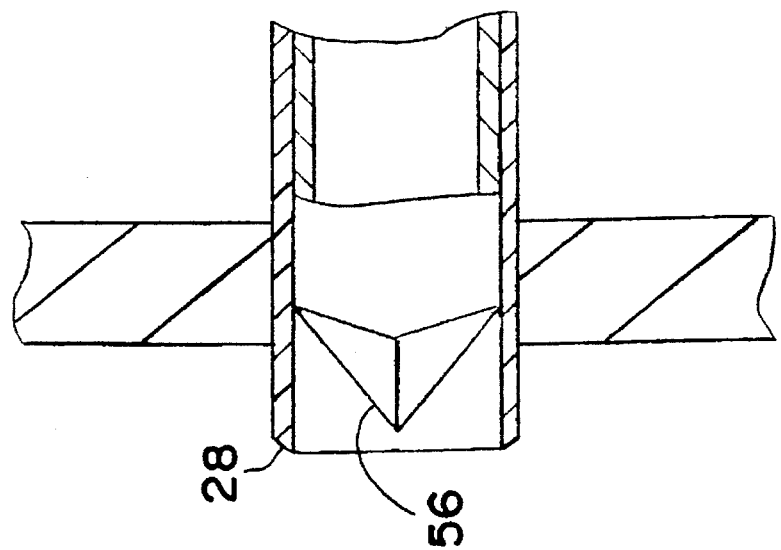

When the sharp distal end 56 of the penetrating member is brought into contact with the anatomical cavity wall W, as shown in FIG. 4, the penetrating member 50 moves proximally against the bias of spring 74 until flange 62 abuts stop 66 such that junction 60 at the distal end of the penetrating member is aligned with the distal end 28 of the portal sleeve. Additionally, proximally movement of penetrating member 50 causes operating member 128 to engage leg 114 of trigger 112 causing the trigger to rotate clockwise to allow the operating member to pass thereby. The clockwise pivotal movement of trigger 112 does not cause movement of the latch 106 since trigger leg 114 is free to pivot clockwise without engaging arm 104. Once the operating member passes by leg 114, spring 118 returns the trigger to the normal position with leg 114 abutting protrusion 120 and extending into slot 130. Accordingly, as penetration of the anatomical cavity wall W is commenced, the force to penetrate is limited to the force required to cause sharp distal end 56 and portal sleeve 26 to pass through the cavity wall since spring 44 has previously been compressed manually by movement of handle 70. That is, during penetration, no force is required to overcome the bias of spring 44. As penetration continues, the safety penetrating instrument will advance through the cavity wall W to the position shown in FIG. 5 wherein the penetrating member 50 has passed entirely through the anatomical cavity wall and begins to move distally under the force of spring 74. As the penetrating member moves distally, the operating member 128 engages trigger leg 114 causing the trigger to pivot counterclockwise looking at FIG. 5 and causing leg 114 to engage protrusion 120 moving arm 104 toward base 98 against the force of spring strip 96. The movement of arm 104 away from the longitudinal axis of the safety penetrating instrument causes latch 106 to move out of engagement with flange 40 on the portal sleeve thereby allowing spring 44 to move the portal sleeve distally to the extended position where distal end 28 protrudes beyond the sharp distal tip 56 of the penetrating member as illustrated in FIG. 6 thereby protecting tissue within the anatomical cavity from inadvertent contact with the sharp distal tip 56. With the distal end 28 of the portal sleeve in the anatomical cavity, the penetrating unit 24 can be withdrawn from the portal unit 22 leaving the portal sleeve in place such that instruments for performing endoscopic procedures can be introduced into the cavity via the portal formed by the portal unit.

By forming spring 44 to be relatively strong, protrusion of the portal sleeve is assured even though the portal sleeve engages the tissue of the anatomical cavity wall W or tissue is jammed between the portal sleeve and the penetrating member. Additionally, the strong force of spring 44 provides the surgeon with the psychological benefit of knowing the portal sleeve is protecting the penetrating member. Should tissue within the anatomical cavity be contacted by the distal end 28 of the portal sleeve, the portal sleeve can bounce or give a little in the manner of shock absorber to protect such contacted tissue. The strong force of spring 44 also provides the surgeon with an easily felt tactile signal that the portal sleeve has moved to the extended position and that penetration into the cavity has occurred. When flange 40 moves along with the portal sleeve to the extended position, lock 86 will be received in slot 42 to hold the portal sleeve in the extended position. The locking effect provided by lock 86 can be varied dependent upon the angle of surface 88 in that the closer surface 88 is to an angle transverse to the longitudinal axis of the safety penetrating instrument, the more securely locked will be the portal sleeve.

Figure 7:
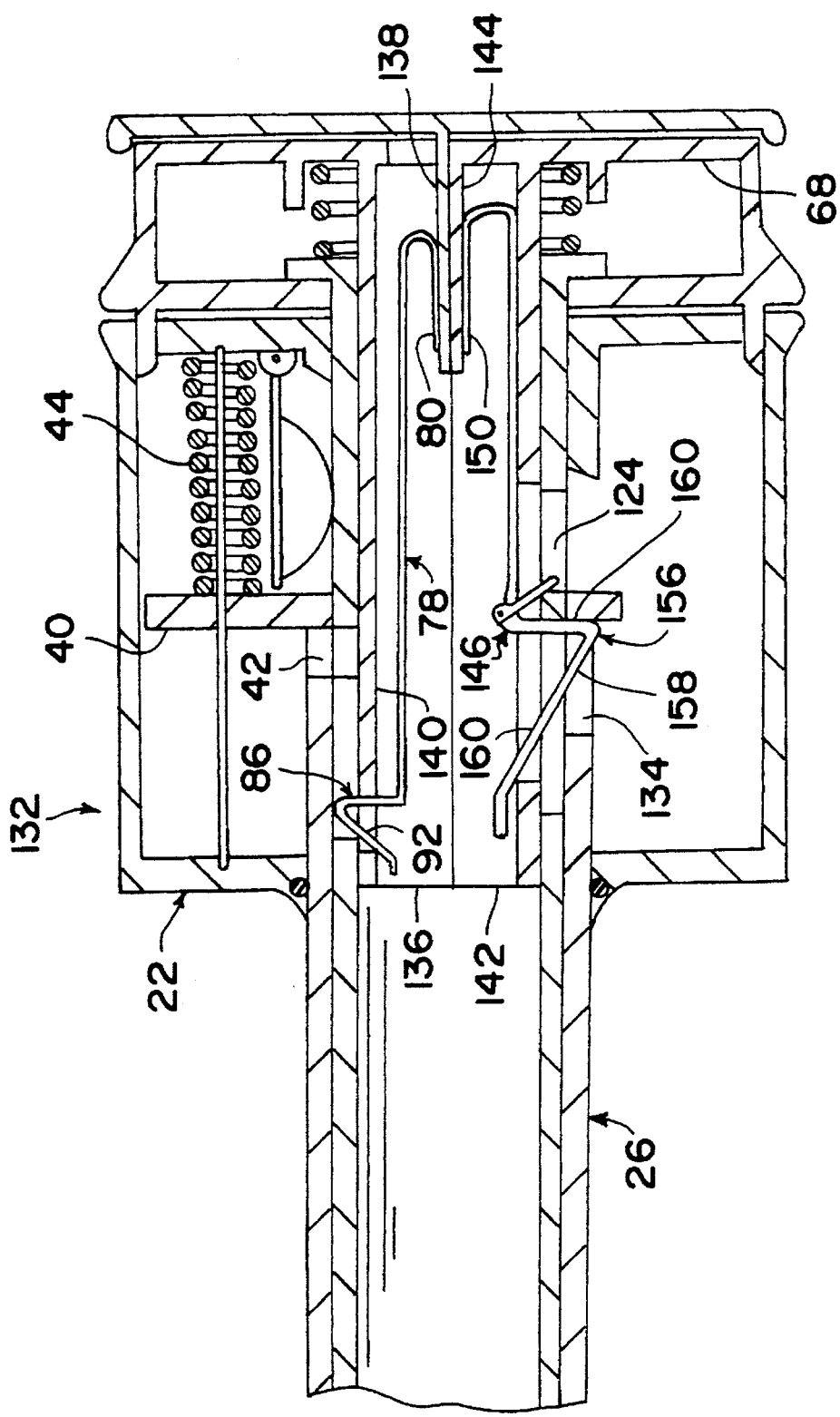
FIG. 7 is a broken longitudinal section of another embodiment of a safety penetrating instrument according to the present invention.

Another embodiment of a safety penetrating instrument 132 according to the present invention is shown in FIG. 7 with the primary difference between safety penetrating instruments 20 and 132 being that the locking and releasing mechanism is disposed within a tubular extension from the hub closer to the longitudinal axis of the safety penetrating instrument. Portal unit 22 is substantially identical to the portal unit of safety penetrating instrument 20 with the exception that portal sleeve 26 includes a slot or notch 134 adjacent flange 40 and opposite slot or notch 42. The primary difference in the penetrating unit 24 is that the guide tube is formed of a semi-tubular support member 136 extending distally from handle 70 having a lower wall 138 mounting the base 80 of locking member 78 and an upper wall 140 having slot 92 therein for receiving lock 86. A semi-tubular support member 142 extends from rear hub wall 68 and has an upper wall 144 mounting a locking and releasing mechanism 146. Support members 136 and 142 form, together, a tubular guide structure having the configuration of guide tube 72 in safety penetrating instrument 20 such that penetrating member 50 slides therealong.

Figure 8:
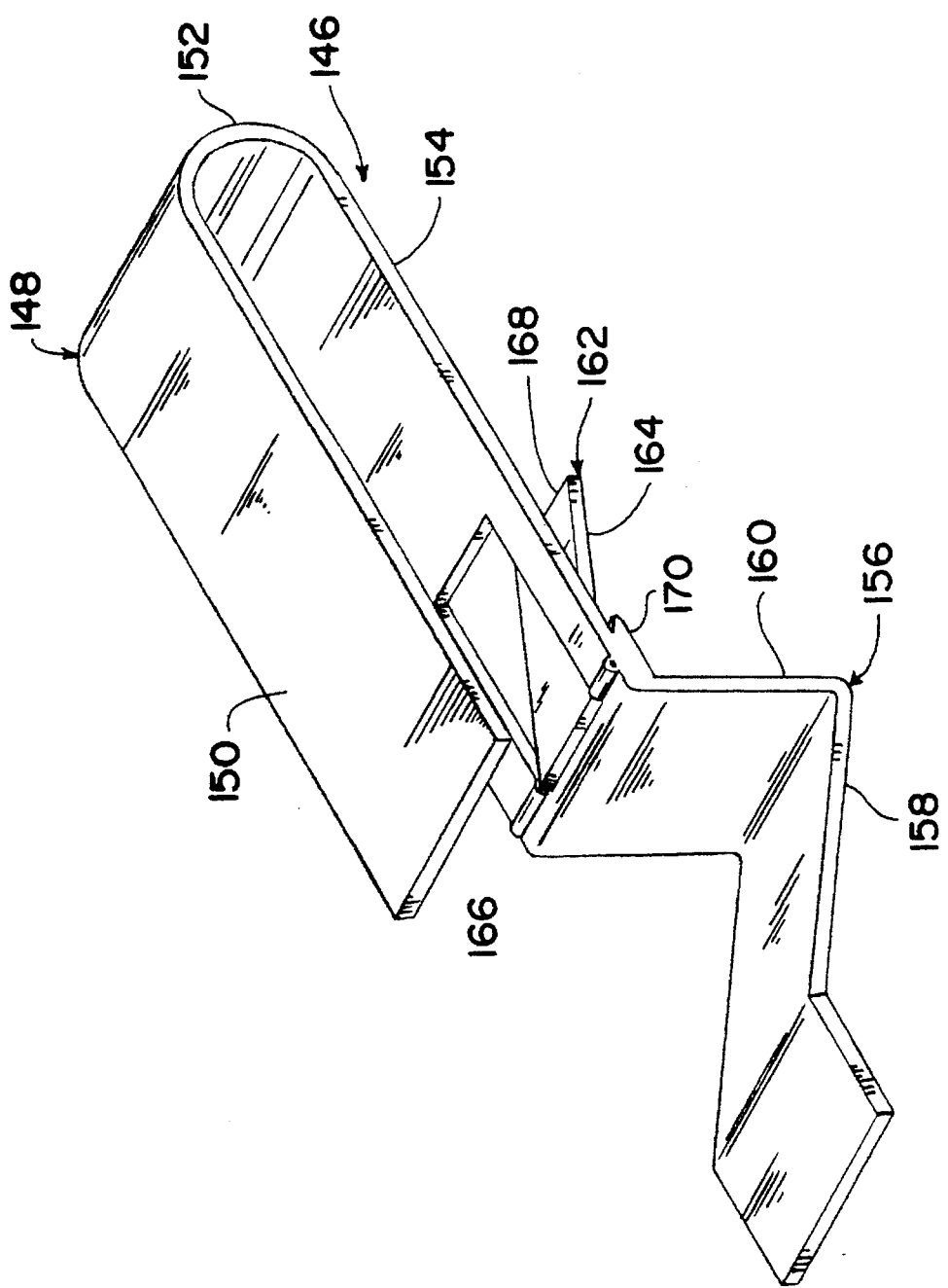
FIG. 8 is a perspective view of the locking and releasing mechanism of the safety penetrating instrument of FIG. 7.

The locking and releasing mechanism 146 for locking the portal sleeve in a retracted position exposing the sharp distal end 56 of the penetrating member and for releasing the portal sleeve to allow the portal sleeve to return to the extended position protruding beyond the distal end of the penetrating member includes, as shown in FIG. 8, a latch or locking spring 148 made of a strip of resilient material formed to have a base 150 mounted on wall 144 of support member 142 and a bend 152 joining the base with an arm 154 spaced from the base. Arm 154 carries a protruding latch 156 having a distal angled surface 158 joining a proximal latching surface 160 disposed substantially transversely to the longitudinal axis of the safety penetrating instrument and substantially parallel to the portal sleeve flange 40. Latch 156 extends through a slot 160 in support member 142 to be received in slot 134 in portal sleeve 26 when the portal sleeve is in the locked retracted position. A trigger 162 is formed by a leg 164 having an end pivotally mounted on a pin 166 on arm 154, and an opposing end 168 of leg 164 extends angularly, proximally from arm 154 through slot 160 in support member 142 to be received in slot 124 in penetrating member 50. Locking spring 148 carries a protrusion 170 disposed adjacent the pivoted end of leg 164 of trigger 162 to limit clockwise pivotal movement of the trigger away from arm 154 while counterclockwise pivotal movement of the trigger is permitted against the bias of a spring, not shown.

Use of the safety penetrating instrument 132 is essentially the same as that described above with respect to safety penetrating instrument 20 in that proximal movement of handle 70 moves lock 86 proximally to position the portal sleeve in the retracted, locked position shown in FIG. 7. During penetration, proximal movement of the penetrating member will cause operating member 128 to move proximally past trigger 162 such that, upon entry into the anatomical cavity, distal movement of the penetrating member will cause the operating member 128 to engage trigger 162 and move the trigger clockwise against protrusion 170 moving arm 154 toward base 150 and releasing latch 156 from flange 40 to permit spring 44 to move the portal sleeve distally to the extended protruding position.

Figure 9:
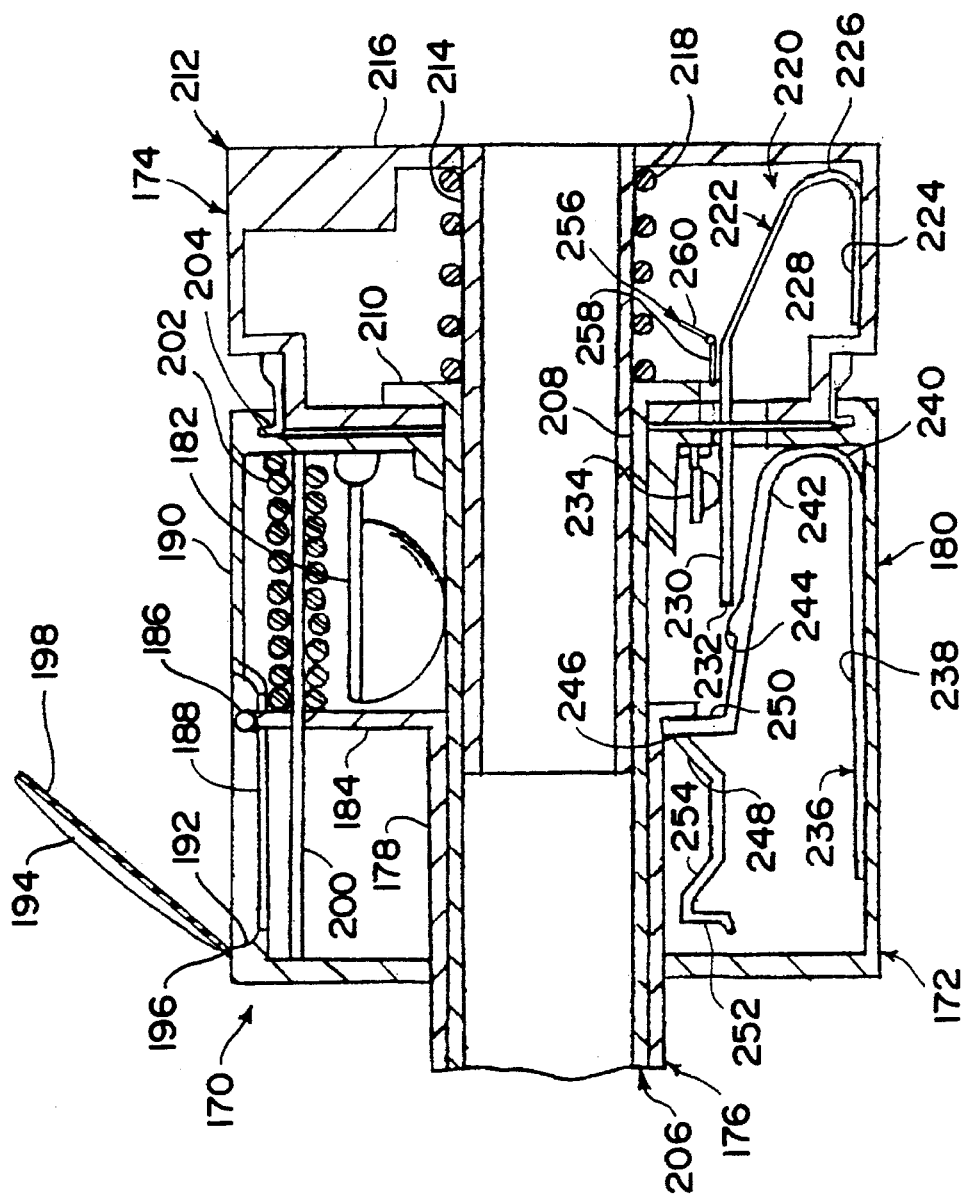
FIG. 9 is a broken longitudinal section of an additional embodiment of a safety penetration instrument according to the present invention.

Another embodiment of a safety penetrating instrument 170 according to the present invention is shown in FIG. 9 with the primary differences between safety penetrating instruments 20 and 170 being that the handle for retracting the portal sleeve extends laterally out of the portal unit housing and the trigger of the locking and releasing mechanism is disposed within the hub of the penetrating unit. Safety penetrating instrument 170 includes a portal unit 172 and a penetrating unit 174. The portal unit 172 includes an elongate cylindrical portal sleeve or cannula 176 having a proximal end 178 slidably received in a housing 180 mounting a valve 182. The proximal end 178 of the portal sleeve carries a transversely extending flange 184, and a handle 186 is mounted on flange 184 and extends through a slot 188 in a top wall 190 of the housing 180, the handle 186 being positioned in an elongate, trough-like recess 192 in the top wall. A transparent cover 194 is pivotally mounted on top wall 190 via a hinge 196 and carries a peripheral gasket or sealing membrane 198 such that, when the cover 194 is pivoted to a closed position abutting top wall 190, gasket 198 seals the housing to prevent fluid flow through the opening formed by slot 188. Flange 184 has a passage therethrough receiving a guide rod 200, and a helical spring 202 is coiled around guide rod 200 and mounted in compression between a rear wall 204 of the housing and flange 184 to bias the portal sleeve distally. The penetrating unit 174 includes an elongate penetrating member 206 having a hollow proximal end 208 terminating at a transversely extending flange 210. A guide tube 214 extends from a rear wall 216 of hub 212 to slidably receive the hollow proximal end 208 of the penetrating member, and a helical spring 218 is coiled around guide tube 214 and mounted in compression between hub rear wall 216 and flange 210 to bias the penetrating member distally.

A locking and releasing mechanism 220 for locking the portal sleeve in a retracted position exposing the sharp distal end of the penetrating member and for releasing the portal sleeve to allow the portal sleeve to return to the extended position beyond the distal end of the penetrating member includes a latch or locking spring 222 made of a strip of resilient material formed to have a substantially flat base 224 secured to a bottom wall of hub 212 and a bend 226 joining the base with an arm 228 spaced from the base. Arm 228 has an extension 230 passing through aligned openings in the front wall of hub 212 and the rear wall of housing 180 to terminate at an end 232. A valve member 234 is mounted adjacent the opening in the rear wall of housing 180 to seal the opening therein closed when the extension 230 is withdrawn therefrom. The locking and releasing mechanism 222 also includes a latch or locking spring 236 made of a strip of resilient material formed to have a substantially flat base 238 secured to a bottom wall of housing 180 and a bend 240 joining the base 238 with an upwardly angled arm 242 spaced from the base. Arm 242 carries a bump 244 disposed adjacent the end 232 of extension 230 and, distally of bump 244, carries a protruding latch 246 having a distal angled surface 248 joining a proximal latching surface 250 disposed substantially transversely to the longitudinal axis of the safety penetrating instrument and substantially parallel to the portal sleeve flange 184. Angled surface 248 leads to a locking finger 252 via a distally angled surface 254. A trigger 256 is juxtaposed with extension 230 of arm 228 and pivotally mounted in the hub on a pin secured to a wall or walls of the hub or a structure supported in the hub, and the trigger is generally L-shaped with a leg 258 overlying extension 230 and a leg 260 extending substantially transversely from leg 258 but at a slight angle toward the proximal end of the safety penetrating instrument. A torsion spring, not shown, is coiled around the pin and fixed to the trigger to bias the trigger counterclockwise looking at FIG. 9 such that leg 258 is biased toward extension 230.

Safety penetrating instrument 170 is illustrated in FIG. 9 with the portal sleeve in the locked, retracted position with flange 184 engaged by latch 246. In use, the portal sleeve is initially in the extended position. In order to move the portal sleeve to the locked, retracted position, cover 194 is pivoted away from housing 180, and handle 186 is grasped and moved proximally such that flange 184 rides over the ramp formed by angled surface 248 to enable latch 246 to engage flange 184. When the penetrating member moves proximally during penetration of an anatomical cavity wall, the operating member formed by flange 210 on the proximal end of the penetrating member will move past trigger 256 by engagement with leg 260 to move the trigger clockwise. Once penetration into the anatomical cavity has been achieved, spring 218 will move the penetrating member distally causing the operating member formed by flange 210 to engage leg 260 pivoting the trigger 256 counterclockwise such that leg 258 engages extension 230 moving the extension toward base 224 and into engagement with bump 244 to, in turn, move arm 242 toward base 238 and move latch 246 out of engagement with flange 184. Accordingly, spring 202 will move the portal sleeve distally to the extended protruding position. As the portal sleeve moves distally, flange 184 will ride over the ramp formed by angled surface 254 allowing locking finger 252 to depress and then move into a locking position holding the portal sleeve in the extended position. Any suitable mechanism can be utilized to disengage the locking finger 252 in order to initiate proximal movement of the portal sleeve to the locked, retracted position.

Figure 10:
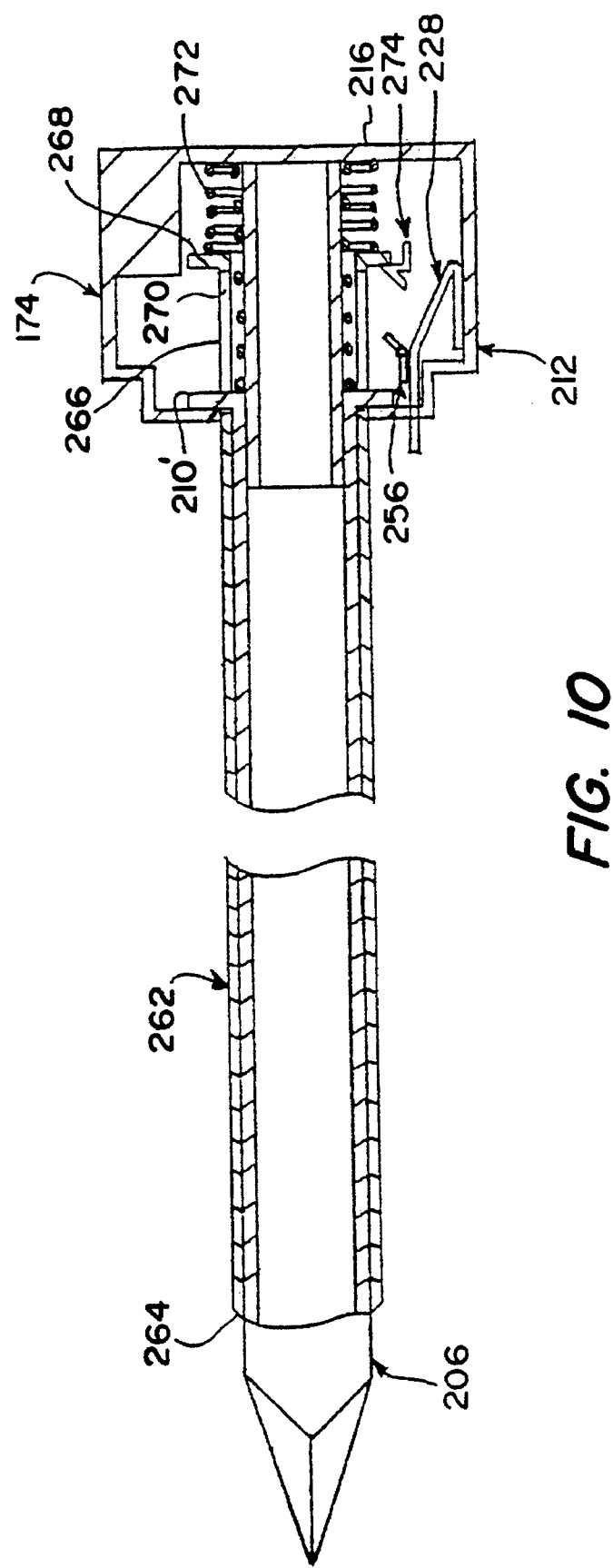
FIG. 10 is a broken longitudinal section of a modification of the safety penetrating instrument of FIG. 9 according to the present invention.

A modification of the safety penetrating instrument 170 of FIG. 9 is illustrated in FIG. 10 with the primary modification being the addition of a protective sheath 262 to the penetrating unit 174. Protective sheath 262 is arranged to move to a protruded position upon withdrawal of the penetrating unit 174 from the portal unit 172. To this end, protective sheath 262 can be formed of any suitable material and has a hollow configuration conforming to the configuration of the penetrating member 206 such that a distal end 264 of the protective sheath protrudes beyond the sharp tip of the penetrating member. Protective sheath 262 has a proximal end 266 received in hub 212 and terminating at a transversely extending flange 268. Slots 270 are formed in the proximal end 266 of the protective sheath to permit movement of flange members 210' extending transversely from the penetrating member, and a helical spring 272 is mounted in compression between flange 268 and the rear wall 216 of hub 212 to bias the protective sheath distally to a protruded position. A lock 274 engages flange 268 to prevent distal movement of the protective sheath, and the lock 274 can be pivoted out of engagement with flange 268 after the penetrating unit is withdrawn from the portal unit allowing the protective sheath 262 to move to the protruded position with flange 268 abutting flange members 210' of the penetrating member.

Release of the portal sleeve to move proximally to the extended position can be triggered by movement of an operating member carried on any member movable in response to the penetrating member entering the anatomical cavity. As described above, the operating member is carried by the penetrating member to limit the number of components in the safety penetrating instrument; however, the operating member could be carried on an additional member movable in response to penetration into the anatomical cavity such as, for example, a probe or rod in or along side of the penetrating member biased to protrude slightly from the distal end of the penetrating member or a hollow member or tube in or around the penetrating member biased to protrude slightly from the distal end of the penetrating member. Various bias means can be used in the safety penetrating instrument to produce movement of the operating member and the safety member including, for example, tension or compression coiled springs, rubber or plastic or magnets.

The components of the safety penetrating instrument of the present invention can be made of any suitable, medical grade materials to permit sterilization for reuse or for single patient use. With respect to the latter, the components can be made of multiple parts of various configurations and materials to reduce cost. The portal unit can have various valves, stop cocks, and seals in the housing to control fluid flow therethrough, and conventional detent mechanisms can be used to connect or latch the hub with the housing when the portal unit and the penetrating unit are assembled.

The locking and releasing mechanisms require only a latch for locking the portal sleeve in the retracted position and a trigger for releasing the latch in response to distal movement of an operating member; and, thus, it will be appreciated that various mechanisms can be employed to produce the locking and releasing functions such as, for example, multiple movably or pivotally mounted cams or pawls. Various locking and releasing mechanisms that can be simply modified for use in the safety penetrating instrument of the present invention are disclosed in applicant's pending applications Ser. No. 07/800,507, filed Nov. 27, 1991, Ser. No. 07/805,506, filed Dec. 6, 1991, Ser. No. 07/808,325, filed Dec. 16, 1991, Ser. No. 07/848,838, filed Mar. 10, 1992, Ser. No. 07/868,566 and Ser. No. 07/868,578 filed Apr. 15, 1993, Ser. No. 07/929,338, filed Aug. 14, 1992 and Ser. No. 07/845,177, filed Sep. 15, 1992, the disclosures of which are incorporated herein by reference. The above applications disclose automatically retracting safety penetrating instruments such that modification of the locking and releasing mechanisms requires configuring the latches to lock a member in a retracted position rather than an extended position. The above applications also disclose various bias arrangements useful with the safety penetrating instrument of the present invention.

From the above, it will be appreciated that the safety penetrating instrument of the present invention permits use of strong bias springs to assure movement of a safety member formed by a portal sleeve to the extended, protective position without increasing the force to penetrate. The features of the various embodiments described above can be combined in any manner desired dependent upon the requirements and complexity of the safety penetrating instrument.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A safety penetrating instrument for establishing a portal in a wall of an anatomical cavity for performing endoscopic procedures comprising an elongate, tubular portal sleeve for introducing medical instruments into the anatomical cavity, said portal sleeve having a distal end for positioning in the anatomical cavity and a proximal end for positioning externally of the anatomical cavity wall;

a penetrating member disposed in said portal sleeve and having a distal end for penetrating tissue said penetrating member being removable from said portal sleeve;

housing means receiving said portal sleeve proximal end for mounting said portal sleeve to be movable relative to said housing means between an extended position where said portal sleeve distal end protrudes distally from said penetrating member distal end and a retracted position where said portal sleeve distal end is disposed proximally of said penetrating member distal end to expose said penetrating member distal end;

bias means for biasing said portal sleeve to move distally toward said extended position and for permitting said portal sleeve to move proximally toward said retracted position;

handle means coupled with said portal sleeve for manually moving said portal sleeve proximally to said retracted position;

locking means for engaging said portal sleeve to lock said portal sleeve in said retracted position; and releasing means responsive to entry of said safety penetrating instrument into the anatomical cavity for triggering release of said locking means to permit said bias means to move said portal sleeve to said extended position.

2. A safety penetrating instrument as recited in claim 1 wherein said handle means extends from said housing means and said locking means is disposed in said housing means at a position to automatically lock said portal sleeve in said retracted position when said portal sleeve is manually moved to said retracted position by said handle means.

3. A safety penetrating instrument as recited in claim 1 wherein said housing means includes a wall having a slot therein and said handle means includes a pin extending through said slot to terminate at a handle external of said housing means to be visible.

4. A safety penetrating instrument as recited in claim 3 wherein said handle means includes a transparent cover disposed over said slot and said handle in sealing engagement with said wall of said housing means.

5. A safety penetrating instrument as recited in claim 1 wherein said safety penetrating instrument has a longitudinal axis, said housing means includes a rear wall with a passage therethrough and said handle means includes a member extending through said passage for movement substantially along said longitudinal axis of said safety penetrating instrument.

6. A safety penetrating instrument as recited in claim 5 wherein said penetrating member has a proximal end and further comprising hub means receiving said penetrating member proximal end and having a rear wall with a passage therethrough, said handle means member extending through said hub means passage and being coupled with said penetrating member proximal end.

7. A safety penetrating instrument as recited in claim 6 wherein said penetrating member proximal end is hollow and said handle means member is received in said penetrating member proximal end.

8. A safety penetrating instrument as recited in claim 7 wherein said penetrating member proximal end has a slot therein and said handle means includes a spring latch mounted on said handle means member for engagement and disengagement with said slot.

9. A safety penetrating instrument as recited in claim 1 wherein said handle means extends from said housing means and further comprising sealing means for preventing fluid flow from said housing means adjacent said handle means.

10. A safety penetrating instrument as recited in claim 1 and further comprising a protective sheath surrounding said penetrating member and having a distal end, and protective sheath bias means for biasing said protective sheath to move to an extended position where said protective sheath distal end protrudes beyond said penetrating member sharp distal end.

11. A safety penetrating instrument as recited in claim 10 wherein said penetrating member has a proximal end and said protective sheath has a proximal end and further comprising hub means receiving said penetrating member proximal end, said protective sheath proximal end and said protective sheath bias means whereby said hub means, said penetrating member and said protective sheath can be withdrawn from said safety penetrating instrument with said protective sheath distal end protruding beyond said penetrating member sharp distal end.

12. A safety penetrating instrument as recited in claim 1 and further comprising hub means mounting said penetrating member and penetrating member bias means biasing said penetrating member distally and permitting proximal movement of said penetrating member with respect to said hub means and wherein said releasing means includes an operating member coupled with said penetrating member for triggering release of said locking means when said penetrating member bias means moves said penetrating member distally upon penetration into the anatomical cavity.

13. A safety penetrating instrument as recited in claim 1 and further comprising means for locking said portal sleeve in said extended position.

14. A safety penetrating instrument for establishing a portal in a wall of an anatomical cavity for performing endoscopic procedures comprising an elongate, tubular portal sleeve for introducing medical instruments into the anatomical cavity, said portal sleeve having a distal end for positioning in the anatomical cavity and a proximal end for positioning externally of the anatomical cavity wall;

a penetrating member disposed in said portal sleeve and having a distal end for penetrating tissue and a proximal end said penetrating member being removable from said portal sleeve;

hub means receiving said penetrating member proximal end;

penetrating member bias means for biasing said penetrating member distally relative to said hub means and permitting proximal movement of said penetrating member relative to said hub means in response to a force on said penetrating member distal end;

housing means receiving said portal sleeve proximal end for mounting said portal sleeve to be movable relative to said housing means between an extended position where said portal sleeve distal end protrudes distally from said penetrating member distal end and a retracted position where said portal sleeve distal end is disposed proximally of said penetrating member distal end to expose said penetrating member distal end;

portal sleeve bias means for biasing said portal sleeve to move distally toward said extended position and for permitting said portal sleeve to move proximally toward said retracted position;

locking means for engaging said portal sleeve to lock said portal sleeve in said retracted position; and releasing means responsive to entry of said safety penetrating instrument into the anatomical cavity for triggering release of said locking means to permit said portal sleeve bias means to move said portal sleeve to said extended position.

15. A safety penetrating instrument as recited in claim 14 wherein said releasing means includes an operating member carried by said penetrating member for triggering release of said locking means upon said penetrating member bias means moving said penetrating member distally when said penetrating member enters the anatomical cavity.

16. A safety penetrating instrument as recited in claim 15 and further comprising a protective sheath surrounding said penetrating member and having a distal end, and protective sheath bias means for biasing said protective sheath to move to an extended position where said protective sheath distal end protrudes beyond said penetrating member sharp distal end.

17. A safety penetrating instrument for establishing a portal in a wall of an anatomical cavity for performing endoscopic procedures comprising an elongate, tubular portal sleeve for introducing medical instruments into the anatomical cavity, said portal sleeve having a distal end for positioning in the anatomical cavity and a proximal end for positioning externally of the anatomical cavity wall;

a penetrating member disposed in said portal sleeve and having a distal end for penetrating tissue said penetrating member being removable from said portal sleeve;

housing means receiving said portal sleeve proximal end for mounting said portal sleeve to be movable relative to said housing means between an extended position where said portal sleeve distal end protrudes distally from said penetrating member distal end and a retracted position where said portal sleeve distal end is disposed proximally of said penetrating member distal end to expose said penetrating member distal end;

bias means for biasing said portal sleeve to move distally toward said extended position and for permitting said portal sleeve to move proximally toward said retracted position;

locking means for engaging said portal sleeve to lock said portal sleeve in said retracted position; and releasing means including an operating member movable distally responsive to entry of said safety penetrating instrument into the anatomical cavity for triggering release of said locking means to permit said bias means to move said portal sleeve to said extended position.

* * * * *